US00PP26012P2

(12) United States Plant Patent
van Veen

(10) Patent No.: US PP26,012 P2
(45) Date of Patent: Oct. 20, 2015

(54) ***ASTILBE* PLANT NAMED 'VISION INFERNO'**

(50) Latin Name: ***Astilbe arendsii*×*Astilbe chinensis***
Varietal Denomination: Vision Inferno

(71) Applicant: Wilhelmus Franciscus van Veen, Noorden (NL)

(72) Inventor: Wilhelmus Franciscus van Veen, Noorden (NL)

(73) Assignee: Future Plants Licentie B.V., Lisserbroek (NL)

( * ) Notice: Subject to any disclaimer, the term of this patent is extended or adjusted under 35 U.S.C. 154(b) by 168 days.

(21) Appl. No.: 13/998,306

(22) Filed: Oct. 18, 2013

(51) Int. Cl.
*A01H 5/02* (2006.01)

(52) U.S. Cl.
USPC ..... Plt./407

(58) Field of Classification Search
USPC ..... Plt./407
See application file for complete search history.

*Primary Examiner* — Anne Grunberg
(74) *Attorney, Agent, or Firm* — C. A. Whealy

(57) ABSTRACT

A new and distinct cultivar of *Astilbe* plant named 'Vision Inferno', characterized by its broadly upright and strong plant habit; strong and healthy foliage; freely and uniformly flowering habit with large dense inflorescences positioned above the foliar plane; flowers that are white and blushed with pink in color; and good garden performance.

3 Drawing Sheets

Botanical designation: *Astilbe arendsii*×*Astilbe chinensis*.
Cultivar denomination: 'VISION INFERNO'.

BACKGROUND OF THE INVENTION

The present invention relates to a new and distinct cultivar of *Astilbe* plant, botanically known as *Astilbe arendsii*× *Astilbe chinensis* and hereinafter referred to by the name 'Vision Inferno'.

The new *Astilbe* plant is a product of a planned breeding program conducted by the Inventor in Noorden, The Netherlands. The objective of the breeding program was to create new uniform and strong *Astilbe* plants with attractive leaf and flower coloration.

The new *Astilbe* plant originated from a cross-pollination made by the Inventor during the summer of 2005 in Noorden, The Netherlands, of *Astilbe arendsii* 'Weisse Gloria', not patented, as the female, or seed, parent with *Astilbe chinensis* 'Vision in Pink', disclosed in U.S. Plant Pat. No. 11,860, as the male, or pollen, parent. The new *Astilbe* plant was discovered and selected by the Inventor as a single flowering plant within the progeny of the stated cross-pollination in a controlled environment in Noorden, The Netherlands in July, 2006.

Asexual reproduction of the new *Astilbe* plant by divisions in a controlled environment in Noorden, The Netherlands since 2006, has shown that the unique features of this new *Astilbe* plant are stable and reproduced true to type in successive generations.

SUMMARY OF THE INVENTION

Plants of the new *Astilbe* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Vision Inferno'. These characteristics in combination distinguish 'Vision Inferno' as a new and distinct *Astilbe* plant:

1. Broadly upright and strong plant habit.
2. Strong and healthy foliage.
3. Freely and uniformly flowering habit with large dense inflorescences positioned above the foliar plane.
4. Flowers that are white and blushed with pink in color.
5. Good garden performance.

Plants of the new *Astilbe* differ primarily from plants of the female parent. 'Weisse Gloria', in the following characteristics:

1. Inflorescences of plants of the new *Astilbe* are taller than inflorescences of plants of 'Weisse Gloria'.
2. Plants of the new *Astilbe* and 'Weisse Gloria' differ slightly in flower color as plants of 'Weisse Gloria' have light pink-colored flowers.

Plants of the new *Astilbe* differ primarily from plants of the male parent, 'Vision in Pink', in the following characteristics:

1. Inflorescences of plants of the new *Astilbe* are taller than inflorescences of plants of 'Vision in Pink'.
2. Plants of the new *Astilbe* and 'Vision in Pink' differ in flower color as plants of 'Vision in Pink' have bright pink-colored flowers.

Plants of the new *Astilbe* can be compared to plants of *Astilbe arendsii* 'Gloria', not patented. In side-by-side comparisons conducted in Noorden, The Netherlands, plants of the new *Astilbe* differed from plants of 'Gloria' in the following characteristics:

1. Inflorescences of plants of the new *Astilbe* were larger and denser than inflorescences of plants of 'Gloria'.
2. Plants of the new *Astilbe* and 'Gloria' differed in flower color as plants of 'Gloria' had pink-colored flowers.

Plants of the new *Astilbe* can also be compared to plants of *Astilbe arendsii* 'Gloria Purpurea', not patented. In side-by-side comparisons conducted in Noorden, The Netherlands, plants of the new *Astilbe* differed from plants of 'Gloria Purpurea' in the following characteristics:

1. Inflorescences of plants of the new *Astilbe* were larger and denser than inflorescences of plants of 'Gloria Purpurea'.
2. Plants of the new *Astilbe* and 'Gloria Purpurea' differed in flower color as plants of 'Gloria Purpurea' had purple-colored flowers.

BRIEF DESCRIPTION OF THE PHOTOGRAPHS

The accompanying colored photographs illustrate the overall appearance of the new *Astilbe* plant showing the colors as true as it is reasonably possible to obtain in colored reproductions of this type. Colors in the photographs may differ slightly from the color values cited in the detailed botanical description which accurately describe the colors of the new *Astilbe* plant.

The photograph on the first sheet comprises a side perspective view of a typical flowering plant of 'Vision Inferno' grown in a container.

The photograph on the top of the second sheet is a close-up view of typical leaves of 'Vision Inferno'.

The photograph on the third sheet is a close-up view of typical inflorescences of 'Vision Inferno'.

DETAILED BOTANICAL DESCRIPTION

The aforementioned photographs and following observations, measurements and values describe plants grown during the late summer in ground beds and 11-cm containers in an outdoor nursery and in a cold frame greenhouse in Noorden, The Netherlands and under cultural practices typical of commercial production. During the production of the plants, day temperatures ranged from 16° C. to 32° C. and night temperatures ranged from 6° C. to 18° C. Plants were 20 months old when the photographs and description were taken. In the following description, color references are made to The Royal Horticultural Society Colour Chart, 2007 Edition, except where general terms of ordinary dictionary significance are used.

Botanical classification: *Astilbe arendsii*×*Astilbe chinensis* 'Vision Inferno'.

Parentage:

*Female, or seed, parent.*—*Astilbe arendsii* 'Weisse Gloria', not patented.

*Male, or pollen, parent.*—*Astilbe chinensis* 'Vision in Pink', disclosed in U.S. Plant Pat. No. 11,860.

Propagation:

*Type*.—By divisions.

*Time to initiate roots, summer*.—About 30 days at 18° C.

*Time to produce a rooted young plant, summer*.—About eight months at 18° C.

*Root description*.—Fine, moderately fibrous; whitish to greyed orange in color.

*Rooting habit*.—Freely branching; medium density.

Plant description:

*Plant and growth habit*.—Herbaceous perennial; broadly upright and strong plant habit; flowering stems and leaves basal; dense and bushy growth habit; moderately vigorous growth habit; freely and uniformly flowering with numerous flowers on branched panicles positioned above the foliar plane.

*Growth rate*.—Moderate to rapid; from divisions, about 10 months are required to produce fully-grown flowering plants.

*Plant height* (*soil level to top of foliar plane*).—About 41 cm.

*Plant height* (*soil level to top of inflorescences*).—About 72 cm.

*Plant width* (*spread*).—About 44.3 cm.

*Stem description*.—Length: About 40.2 cm. Diameter: About 4 mm. Strength: Strong. Texture: Sparsely pubescent. Color: Close to 144A.

Leaf description:

*Arrangement*.—Alternate; biternately compound.

*Leaf length* (*excluding petiole*).—About 25.6 cm.

*Leaf width*.—About 21.6 cm.

*Lateral leaflet length*.—About 6 cm.

Lateral leaflet width.—About 2.9 cm.

*Terminal leaflet length*.—About 7.4 cm.

*Terminal leaflet width*.—About 4.1 cm.

*Lateral and terminal leaflet shape*.—Elliptic to ovate.

*Lateral and terminal leaflet apex*.—Acute to apiculate.

*Lateral and terminal leaflet base*.—Acute to short attenuate.

*Lateral and terminal leaflet margin*.—Biserrate.

*Lateral and terminal leaflet texture, upper and lower surfaces*.—Pubescent; rough.

*Lateral and terminal leaflet venation pattern*.—Pinnate.

*Lateral and terminal leaflet color*.—Developing leaflets, upper surface: Close to 143A. Developing leaflets, upper surface: Close to 138A to 138B. Fully expanded leaflets, upper surface: Close to N137A to N137B; venation, close to 144B. Fully expanded leaflets, lower surface: Close to between 137B and 147B; venation, close to 144C.

*Leaf petiole length*.—About 13.3 cm.

*Leaf petiole diameter*.—About 2 mm.

*Leaflet petiole length*.—About 1.4 cm.

*Leaflet petiole width*.—About 1 mm.

*Leaf and leaflet petiole texture, upper and lower surfaces*.—Smooth, glabrous.

*Leaf and leaflet petiole color, upper and lower surfaces*.—Close to 143B; towards the base, close to 178B.

Flower description:

*Flower type/habit*.—Numerous single rotate flowers arranged on terminal branched panicles; flowers face upright, outward or downward depending on position on the panicle; panicles dense and triangular in shape; freely and uniformly flowering habit with about 2,500 flowers developing per inflorescence.

*Fragrance*.—Faintly fragrant; sweet and pleasant.

*Natural flowering season*.—Plants begin flowering about ten months after planting and flower continuously from early to late summer in The Netherlands.

*Postproduction longevity*.—Flowers last about ten days on the plant; flowers persistent.

*Inflorescence height*.—About 29.4 cm.

*Inflorescence diameter*.—About 10.2 cm.

*Flower buds*.—Height: About 3 mm. Diameter: About 2 mm. Shape: Ovoid. Color: Close to between 155C and 157D; towards the apex, tinged with close to 65D.

*Flower diameter*.—About 6 mm.

*Flower depth*.—About 4 mm.

*Petals*.—Quantity per flower: Typically five in a single whorl. Length: About 3 mm. Lobe width: About 1 mm. Shape: Lanceolate. Apex: Cleft with acute apices. Margin: Entire. Texture, upper and lower surfaces: Smooth, glabrous. Color: Developing petals, upper and lower surfaces: Close to NN155B tinged with close to 62B to 62D. Fully expanded petals, upper and lower surfaces: Close to NN155B tinged with close to 62B to 62D.

*Sepals*.—Quantity per flower: Typically five in a single whorl, fused towards the base; campanulate-shaped calyx. Length: About 2.5 mm. Width: About 1 mm. Shape: Ovate. Apex: Acute. Margin: Entire. Texture, upper and lower surfaces: Smooth, glabrous. Color: Developing sepals, upper and lower surfaces: Close to between 150D and 157D. Fully developed sepals, upper and lower surfaces: Close to NN155B; towards the apex, tinged with close to 65D.

*Peduncles*.—Length: About 28.3 cm. Diameter: About 3 mm. Angle: Erect; secondary peduncles, close to 35° from vertical. Strength: Strong. Texture: Smooth, glabrous. Color: Close to 143B.

*Pedicels*.—Length: About 1 mm. Diameter: About 0.5 mm. Angle: About 50° from peduncle axis. Strength: Moderately strong. Texture: Smooth, glabrous. Color: Close to N155B.

*Reproductive organs*.—Stamens: Quantity per flower: Five. Filament length: About 2 mm. Filament color: Close to 15A and 62A to 62B. Anther shape: Ovate; basifixed. Anther length: About 0.75 mm. Anther color: Close to NN155B. Pollen amount: Scarce. Pollen color: Close to N155A. Pistils: Quantity per flower: Two. Pistil length: About 1 mm. Style length: About 0.75 mm. Style color: Close to NN155B. Stigma shape: Club-shaped. Stigma color: Close to N155C. Ovary color: Close to N155C and 65D.

*Seeds and fruits*.—Seed and fruit development have not been observed on plants of the new *Astilbe*.

Disease & pest resistance: Plants of the new *Astilbe* have not been noted to be resistant to pathogens and pests common to *Astilbe* plants.

Garden performance: Plants of the new *Astilbe* have been observed to have good garden performance and tolerate rain, wind and high temperatures about 35° C. and to be hardy to USDA Hardiness Zone 5.

It is claimed:

1. A new and distinct *Astilbe* plant named 'Vision Inferno' as illustrated and described.

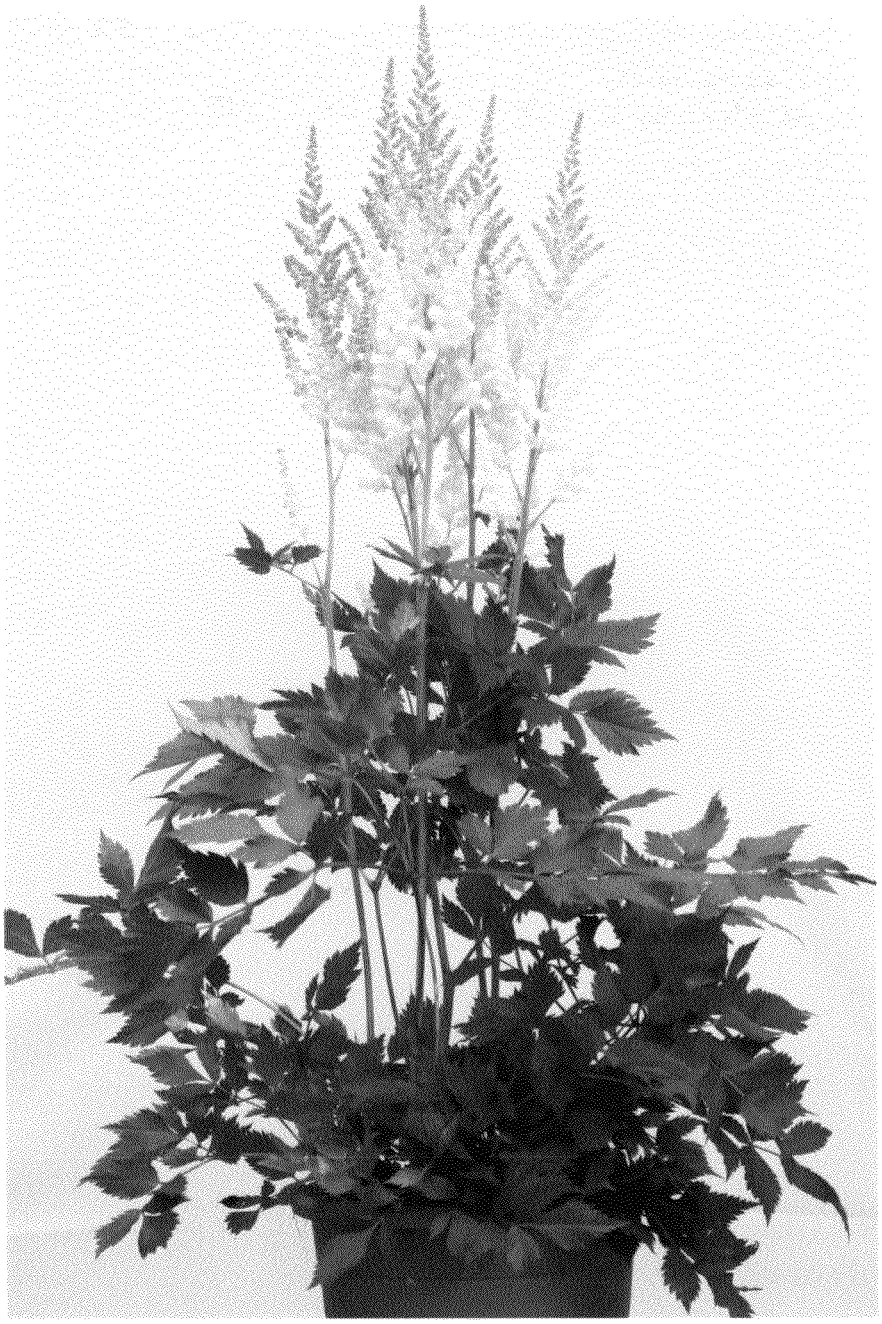

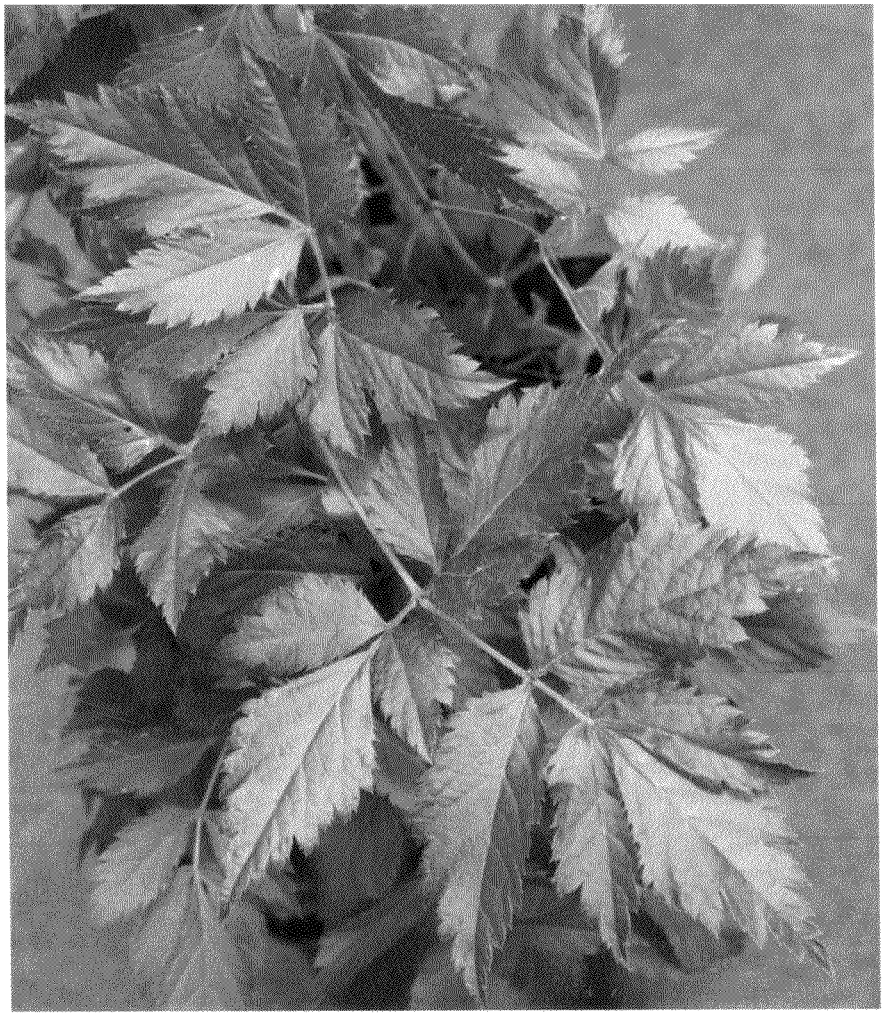

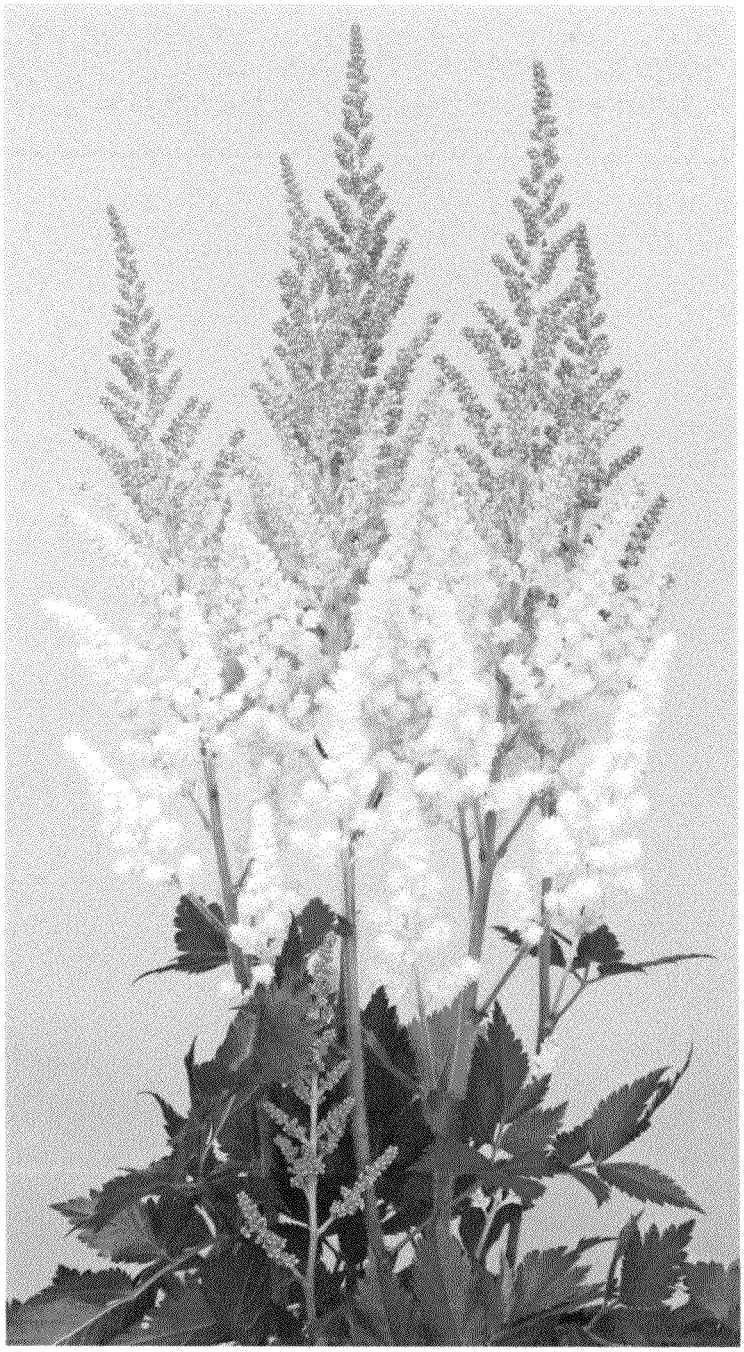

* * * * *